United States Patent
Logan et al.

(10) Patent No.: US 12,090,443 B2
(45) Date of Patent: Sep. 17, 2024

(54) TANGENTIAL FLOW FILTRATION (TFF) SYSTEM AND DISPOSABLE TFF UNIT THAT INCLUDES AN INTEGRATED PUMP APPARATUS

(71) Applicant: FORMULATRIX, INC., Bedford, MA (US)

(72) Inventors: Baker Logan, Bedford, MA (US); Steven Healey, Bedford, MA (US); Dmitry Rodionov, Bedford, MA (US)

(73) Assignee: FORMULATRIX, INC., Bedford, MA (US)

( * ) Notice: Subject to any disclaimer, the term of this patent is extended or adjusted under 35 U.S.C. 154(b) by 1095 days.

(21) Appl. No.: 16/961,022

(22) PCT Filed: Jan. 7, 2019

(86) PCT No.: PCT/US2019/012479
§ 371 (c)(1),
(2) Date: Jul. 9, 2020

(87) PCT Pub. No.: WO2019/139842
PCT Pub. Date: Jul. 18, 2019

(65) Prior Publication Data
US 2021/0060491 A1 Mar. 4, 2021

Related U.S. Application Data

(60) Provisional application No. 62/616,486, filed on Jan. 12, 2018.

(51) Int. Cl.
*B01D 61/18* (2006.01)
*B01D 61/20* (2006.01)
*C07K 1/34* (2006.01)

(52) U.S. Cl.
CPC ............. *B01D 61/18* (2013.01); *B01D 61/20* (2013.01); *C07K 1/34* (2013.01); *B01D 2313/10* (2013.01);
(Continued)

(58) Field of Classification Search
CPC .... B01D 61/18; B01D 61/20; B01D 2319/10; B01D 2319/13; B01D 2319/18; C07K 1/34
(Continued)

(56) References Cited

U.S. PATENT DOCUMENTS 6,544,424 B1 * 4/2003 Shevitz ................. B01D 61/18
210/636
2005/0158851 A1 * 7/2005 Furey ..................... C12M 29/18
435/308.1
(Continued)

FOREIGN PATENT DOCUMENTS

DE    102015122261 B3    1/2017
EP        2714123 A2    4/2014
(Continued)

OTHER PUBLICATIONS

WO2016024058A1 Machine English Translation (Year: 2016).*
(Continued)

*Primary Examiner* — Michael L Hobbs
*Assistant Examiner* — Lenora A Abel
(74) *Attorney, Agent, or Firm* — E. Eric Mills; Todd A. Serbin; Maynard Nexsen PC

(57) ABSTRACT

A tangential flow filtration (TFF) system and disposable TFF unit that includes an integrated pump apparatus is disclosed. Namely, a TFF system is provided that includes a clamp assembly for integrating together a disposable TFF unit, two fluid reservoirs, and an air supply assembly. Further, the disposable TFF unit includes a diaphragm pump assembly
(Continued)

and a concentration membrane. Further, methods of using the TFF system that includes the disposable TFF unit are provided.

16 Claims, 16 Drawing Sheets

(52) U.S. Cl.
CPC ...... *B01D 2313/13* (2013.01); *B01D 2313/18* (2013.01); *B01D 2313/243* (2013.01); *B01D 2315/10* (2013.01); *B01D 2315/16* (2013.01)

(58) Field of Classification Search
USPC ........................................................ 435/283.1
See application file for complete search history.

(56) References Cited

U.S. PATENT DOCUMENTS

| | | | |
|---|---|---|---|
| 2010/0012665 A1 | 1/2010 | Morrissey et al. | |
| 2011/0223583 A1* | 9/2011 | Gordon | A61L 2/24 |
| | | | 435/5 |
| 2014/0342446 A1 | 11/2014 | Pralong et al. | |
| 2015/0041395 A1 | 2/2015 | Oranth et al. | |
| 2015/0190754 A1 | 7/2015 | Harp | |
| 2015/0343332 A1 | 12/2015 | Boyd et al. | |
| 2015/0344921 A1* | 12/2015 | Kacmar | C12P 19/14 |
| | | | 127/2 |
| 2017/0173537 A1* | 6/2017 | Gagnon | B01D 61/18 |

FOREIGN PATENT DOCUMENTS

| | | | |
|---|---|---|---|
| KR | 20150004333 A | 1/2015 | |
| WO | WO-2016024058 A1 * | 2/2016 | ............ B01D 46/24 |
| WO | 2017029305 A1 | 2/2017 | |
| WO | 2017040966 A1 | 3/2017 | |

OTHER PUBLICATIONS

International Search Report and Written Opinion issued in counterpart PCT Application No. PCT/US2019/012479 dated Mar. 4, 2019 (eight (8) pages).

* cited by examiner

TANGENTIAL FLOW FILTRATION (TFF) SYSTEM AND DISPOSABLE TFF UNIT THAT INCLUDES AN INTEGRATED PUMP APPARATUS

CROSS-REFERENCE TO RELATED APPLICATIONS

This application is a 35 U.S.C. § 371 U.S. national phase entry of International Application No. PCT/US2019/012479 filed Jan. 7, 2019, which is related and claims priority to U.S. Provisional Patent Application No. 62/616,486 filed on Jan. 12, 2018; the entire disclosures of which are incorporated herein by reference.

TECHNICAL FIELD

The presently disclosed subject matter relates generally to methods of protein production and more particularly to a tangential flow filtration (TFF) system and disposable TFF unit that includes an integrated pump apparatus.

BACKGROUND

Protein production is a complicated process that involves some combination of the use of biological cells, sub-cellular components, chemical reactions, separation methods, and filtration. The end result of this process (and many intermittent steps) is typically a very dilute solution containing the target protein and small molecules, such as salts, that could not be removed in the previous steps. To continue the purification process or utilize the protein for scientific or industrial purposes, the solution typically requires concentration and buffer exchange. One of the most common methods for this is ultrafiltration.

Ultrafiltration, just like standard filtration, involves a medium (membrane) that is permeable only to some smaller-sized components of the mixture. At the same time, the membrane pore size is chosen such as to be impermeable to the protein of interest. Applying force (typically pressure) to the starting mixture on the sample side of the membrane will cause the smaller components to cross the membrane while leaving the protein on the sample side of the membrane, thus concentrating it. The same principle can be used for buffer exchange by re-suspending the concentrated protein in the desired buffer and repeating the concentration process.

If the sample flow is unidirectional and across the membrane, such filtration setup can be called dead-end filtration. While simple to make and employ, it has a significant downside: it creates a concentration gradient at the membrane as sample mixing relies exclusively on diffusion and convection. Concentration gradients cause decreased filtration flow and create conditions compromising protein stability. Most commonly, dead-end ultrafiltration devices use centrifugal force to create the pressure at the membrane. For example, the solution is put into a tube with the membrane separating the solution from a lower, empty portion of the tube. The tube is spun in the centrifuge so that the solution and small molecules are pushed through the membrane, leaving a small amount of solution and the large protein molecules in the top compartment. This method is tedious for two main reasons: (1) due to the discrete sizes of the filtration devices it is not scalable (i.e., the largest commonly used laboratory device has capacity of fifteen milliliters) and (2) it is difficult to monitor because checking the filtration progress requires stopping the centrifuge. Failure to check the solution to ensure too much is not strained out will result in leaving the protein out of solution and precipitating on the membrane. Furthermore, these centrifuge tubes and membranes cannot be cleaned efficiently. Consequently, these centrifuge tubes and membranes are generally disposed of after only one use.

In contrast to dead-end filtration, tangential flow filtration (TFF) devices have a constant recirculating flow parallel to the membrane on the sample side. TFF (aka, crossflow filtration) is a type of filtration used in the purification of proteins. In TFF, both the pressure and the flow are typically created using a combination of a peristaltic pump and a flow splitter. The membrane types used are identical to dead-end filtration. However, the main advantage of TFF is that the membrane surface is constantly cleared of protein and the solution is mixed so that it has a consistent concentration throughout. The absence of the concentration gradient makes TFF gentler on the proteins and provides better flow characteristics. Other advantages of TFF include ease of online monitoring and scalability. The membranes can be cleaned and reused or disposed of, whereas the tubing and solution containers must be cleaned after being used. The major disadvantage of a traditional TFF setup is its dead volume in the tens of milliliters (caused by the pump and the plumbing), making it not suitable for laboratory-scale use.

Consequently, there is a need for a smaller-scale TFF device that is efficient, consumable, has low dead volume, and can be used and monitored in an automated way to reduce the effort associated with ultrafiltration steps in protein production.

SUMMARY

Disclosed herein is a device, system, and method for tangential flow filtration (TFF) applications. In one embodiment, a TFF system for concentrating a protein solution is described including: a TFF unit having a diaphragm pump assembly and a concentration membrane, the TFF unit is adapted to concentrate proteins from a protein containing solution; an air supply assembly operatively connected to the TFF unit, the TFF unit adapted for air flow control; and a fluid reservoir assembly operatively connected to the TFF unit, the TFF unit adapted for liquid flow control. The air supply assembly may be connected to the TFF unit at one end, and the fluid reservoir assembly may be connected to the TFF unit at an opposing end.

The TFF unit may be disposable and may be adapted for limited use and for smaller volumes of concentration. The TFF unit may have multiple layers. In one embodiment, the multiple layers of the TFF unit may have air channels, fluidic channels, and flow ports for liquid flow control and for air flow control, whereby the diaphragm pump assembly and the concentration membrane are between the outer layers of the multiple layers, and whereby a chamber may be formed between the multiple layers adjacent to the diaphragm pump assembly.

In one example, the multiple layers may include four acrylic layers that are laser bonded, and wherein the diaphragm pump assembly and the concentration membrane are between the two middle layers of the multiple layers.

The diaphragm pump assembly may include a valve component and a diaphragm component adapted to aspirate or dispense protein containing solution through the flow ports. The valve component may have clusters of air actuated valves, including a cluster of three air actuated valves at one end of the diaphragm pump assembly and a cluster of two air actuated valves at an opposing end of the diaphragm pump assembly.

The diaphragm component may include multiple diaphragms. Additionally, the diaphragm component may be a diaphragm that is a domed section larger than the valve component.

The air supply assembly of the TFF system may include an air supply unit and a bank of solenoids adapted to apply positive or negative pressure through the air supply unit to the diaphragm pump assembly.

The fluid reservoir assembly may include two fluid reservoirs, one for containing protein containing solution and the other for containing a buffer solution. Each of the two fluid reservoirs may include a cap mounted with a liquid flow connector and an air flow connector.

The liquid flow connector may include two tubes that extend downward into the contained liquid, one of the two tubes used to aspirate liquid from the fluid reservoir, and the other of the two tubes used to return liquid to the fluid reservoir, and the air flow connector may be common between the two fluid reservoirs.

The TFF system may further include a clamp assembly for holding the TFF unit, the air supply assembly, and the fluid reservoir assembly. In addition, the TFF system may include a volume sensor for measuring liquid level in the fluid reservoir assembly, a waste slide adapted to channel permeate, and a waste container connected to the waste slide adapted to collect the channeled permeate.

The TFF system may also include a unit holder and a clamp handle, the unit holder having slots for aligning the TFF unit, and the clamp handle adapted to force the unit holder and the TFF unit into the clamp assembly so that the TFF unit becomes connected to and sealed with the fluid reservoir assembly and the air supply assembly.

A method of making a TFF system for concentrating a protein solution may include the steps of: providing components to make a TFF system, the components including a disposable TFF unit, a fluid reservoir assembly, an air supply assembly, and a clamp assembly; assembling the TFF system with the components; providing a user interface connected to the TFF system; setting the parameters of a filtration process using the user interface; and initiating the filtration process.

The assembling step may include the steps of: inserting the fluid reservoir assembly into the clamp assembly; locking the disposable TFF unit into the clamp assembly; and connecting the TFF disposable unit to the air supply assembly and the fluid reservoir assembly.

The method may also include the step of introducing an amount of buffer solution and an amount of protein containing solution into the fluid reservoir assembly, whereby the filtration process includes the steps of priming the TFF system with the buffer solution, and concentrating the protein from the protein containing solution.

A method of concentrating a protein solution through TFF may include the steps of: providing a TFF system including a TFF unit having a diaphragm pump assembly and a concentration membrane, the TFF unit adapted to concentrate proteins from a protein containing solution; an air supply assembly operatively connected to the TFF unit; a fluid reservoir operatively connected to the TFF unit, the fluid reservoir containing a buffer solution and a protein containing solution; and a clamp assembly holding the TFF unit, the air supply assembly, and the fluid reservoir; setting pumping sequence parameters for a processing the protein containing solution; begin processing the protein containing solution by initiating a priming pumping sequence; continue processing the protein containing solution by initiating a concentration pumping sequence; continue processing protein solution by initiating diafiltration pumping sequence; and collecting protein retentate from the protein solution.

BRIEF DESCRIPTION OF THE DRAWINGS

Figure 1:
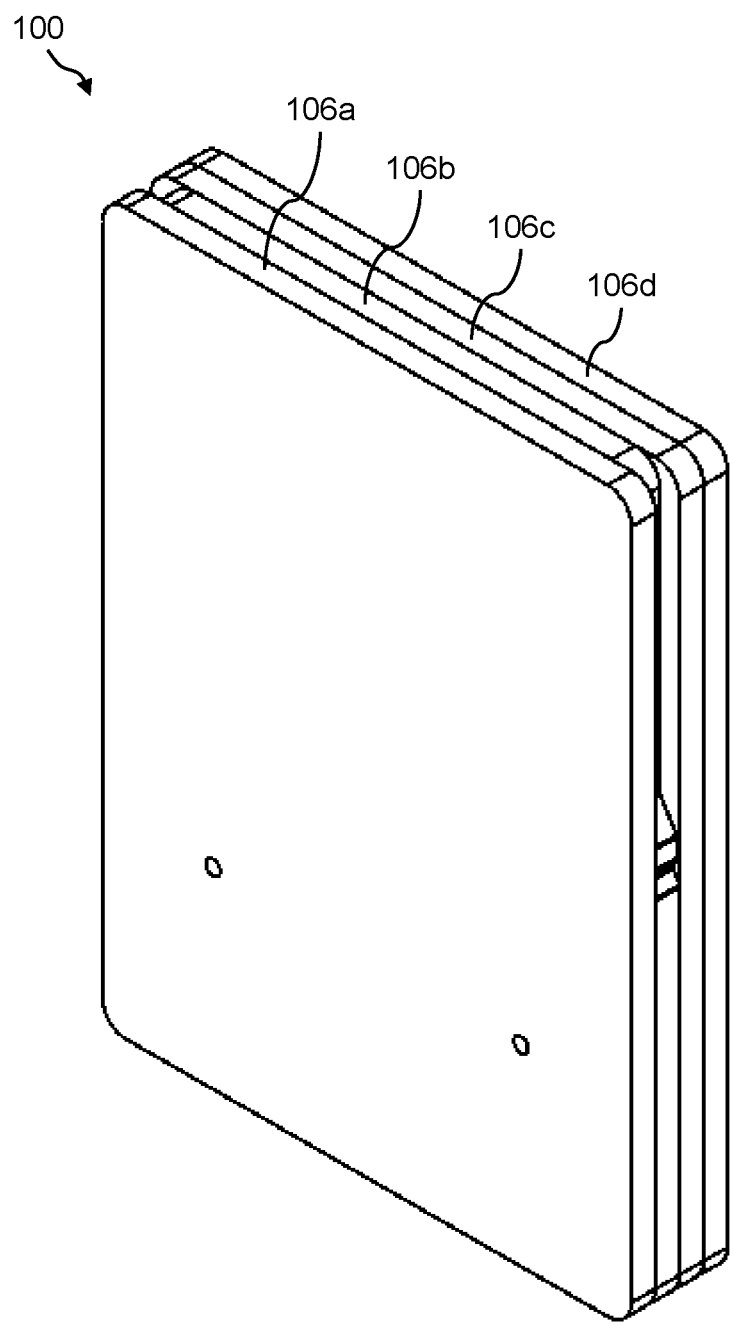
Figure 2:
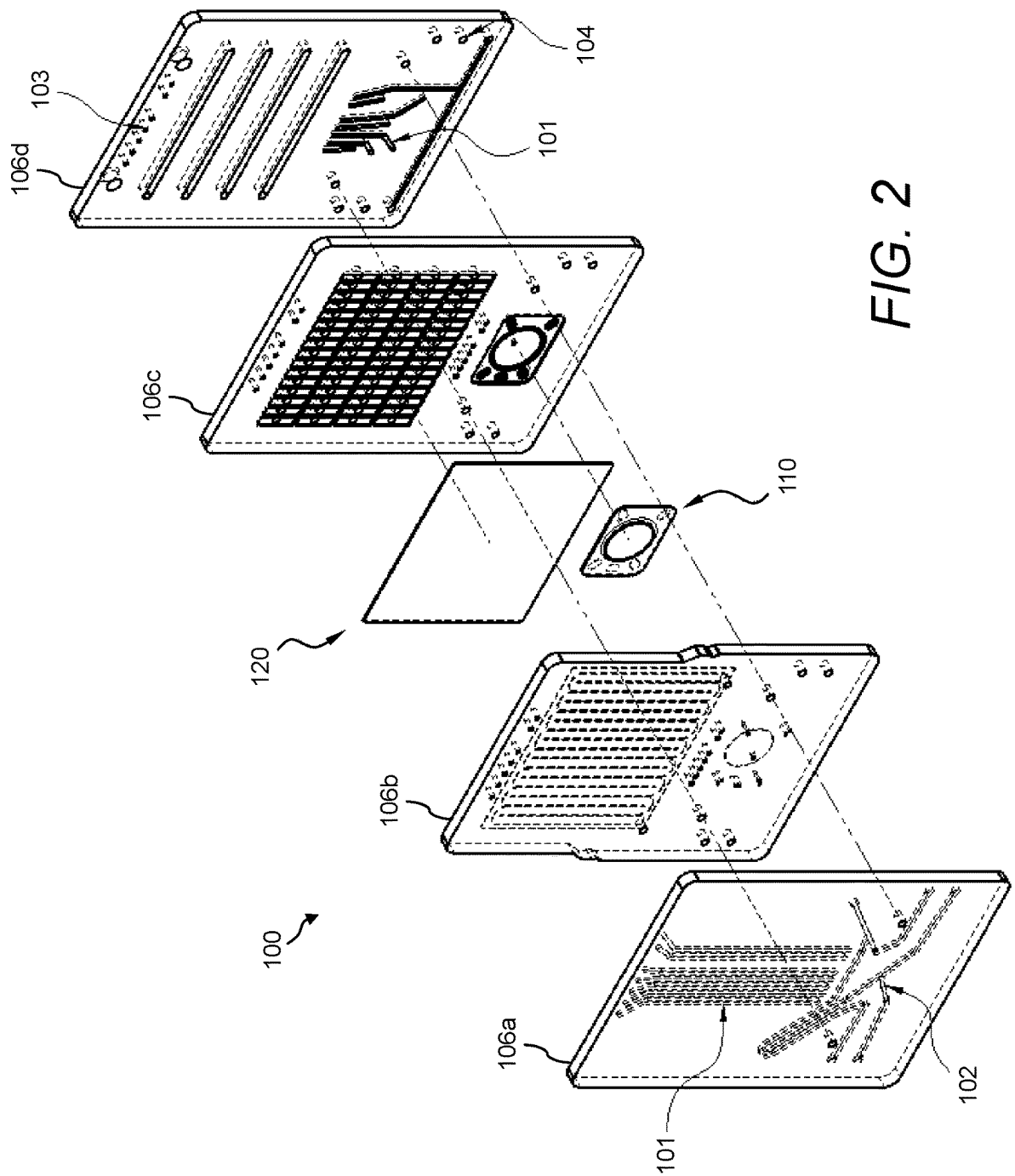
Figure 3:
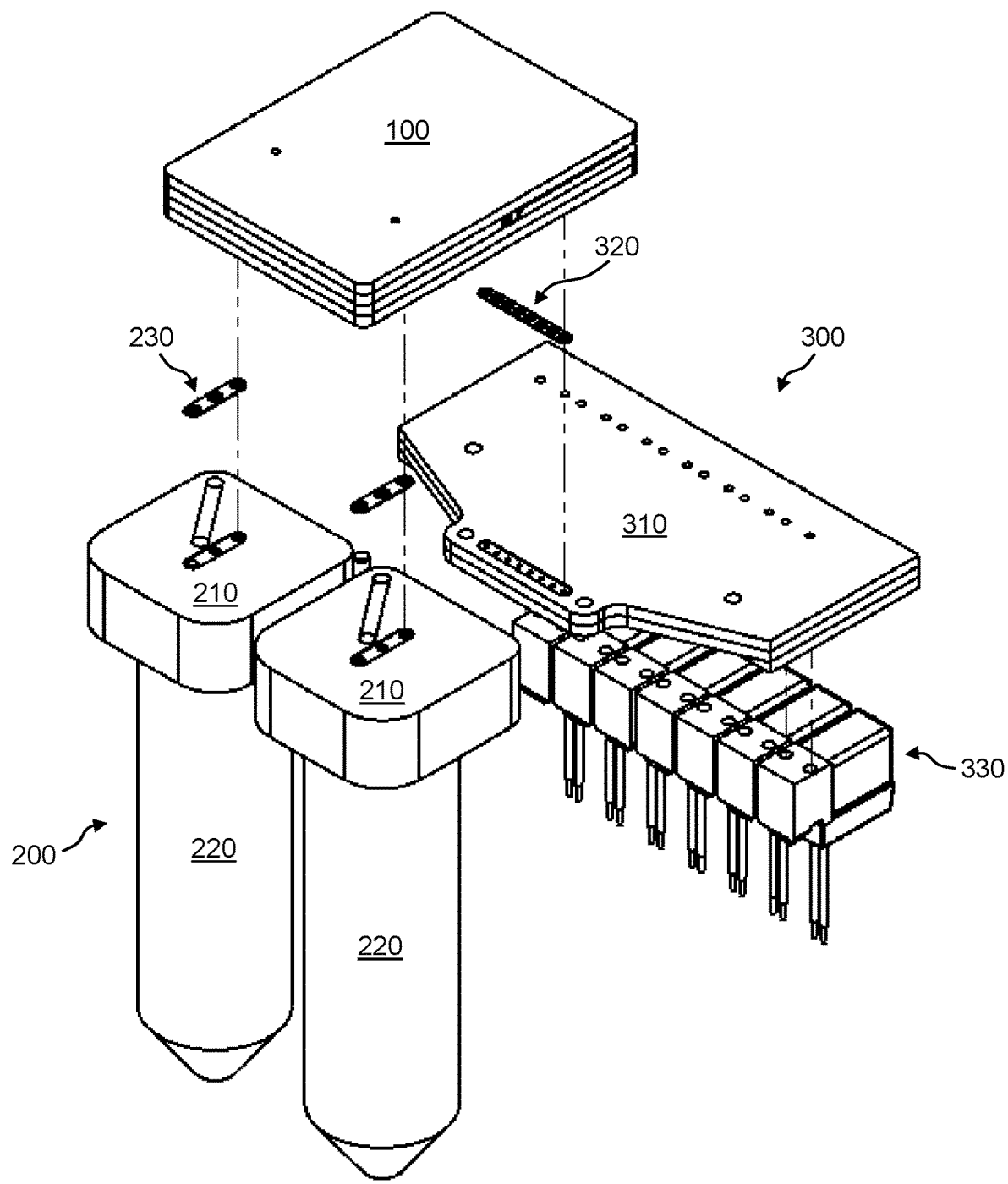
Figure 4:
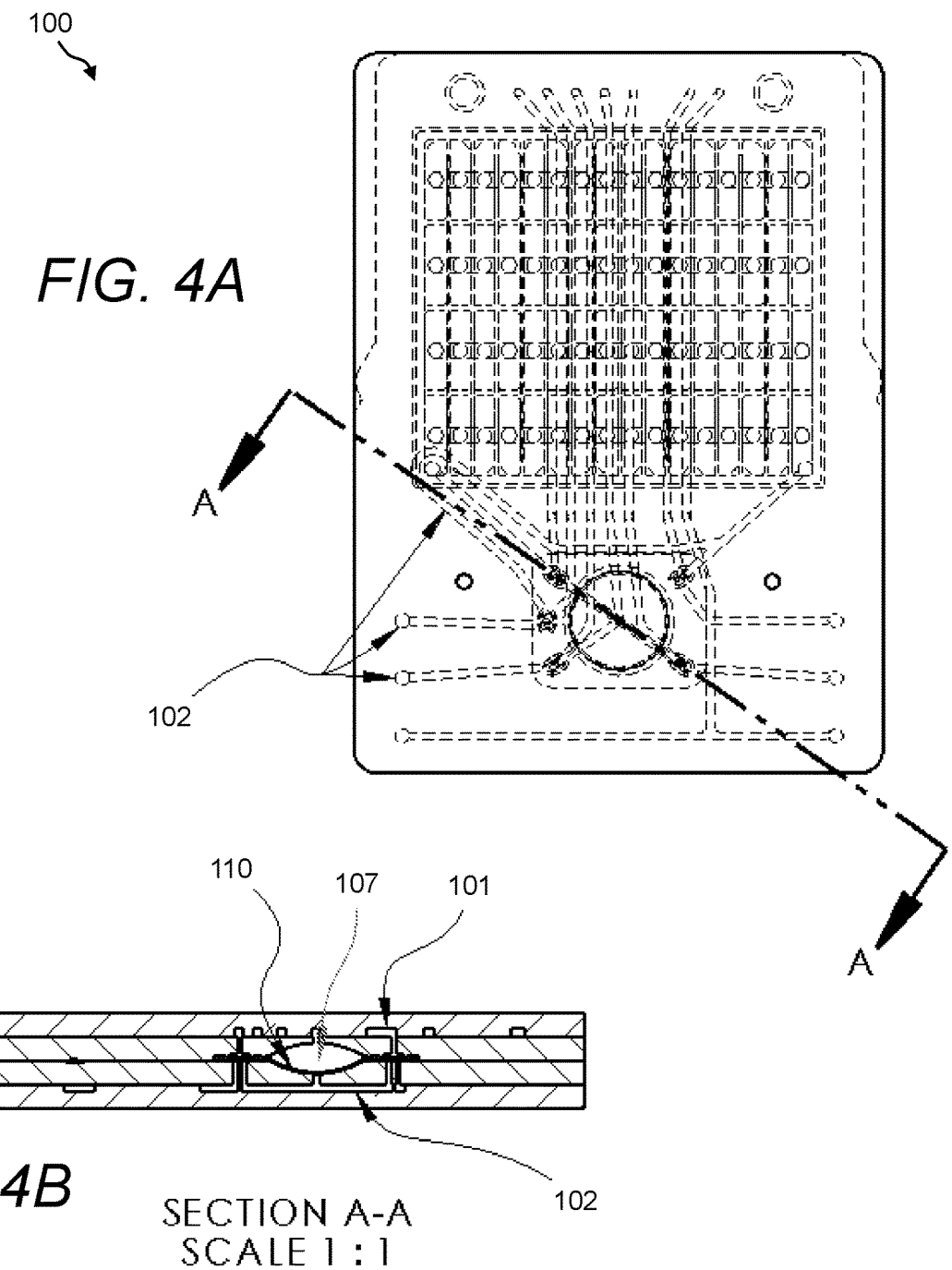
Figure 5:
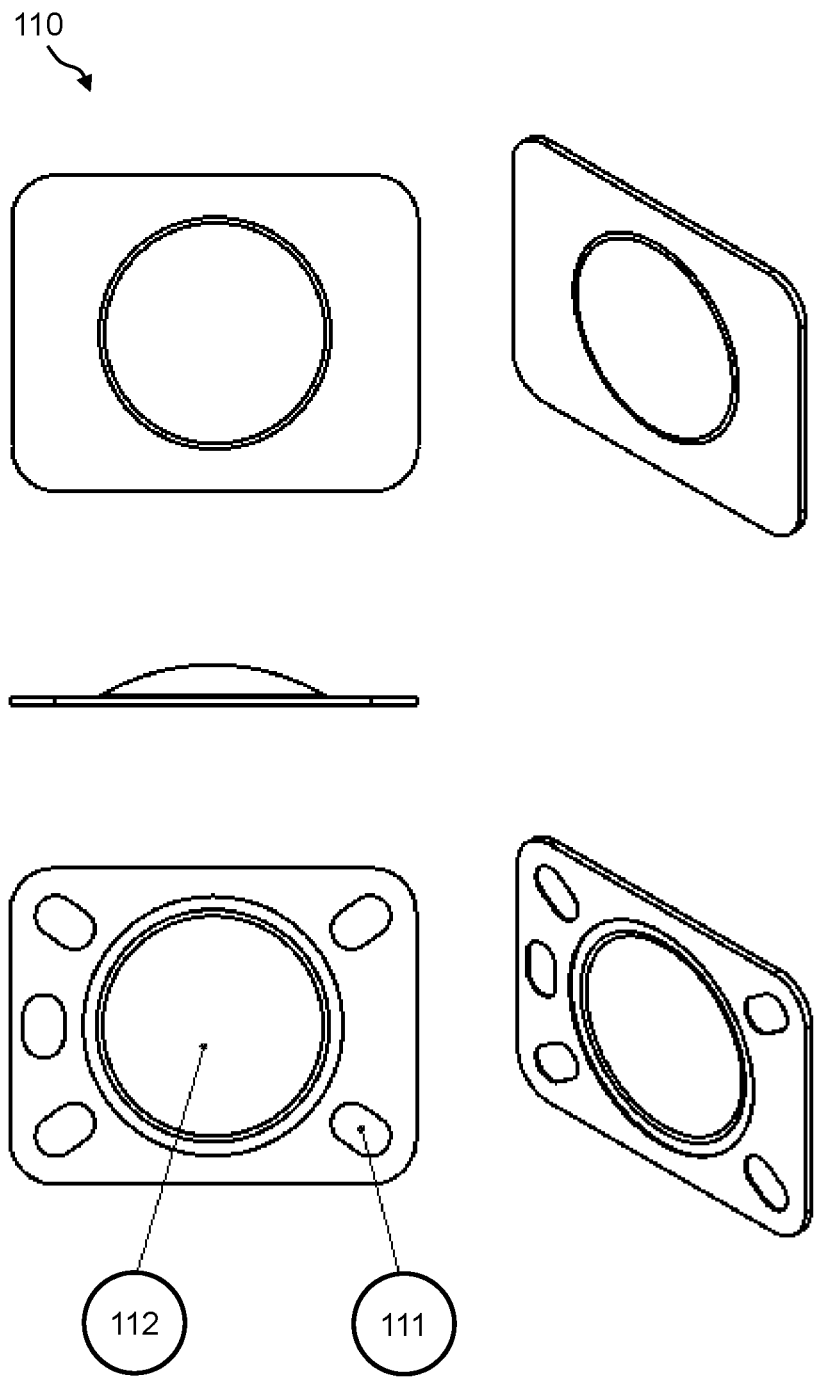
Figure 6:
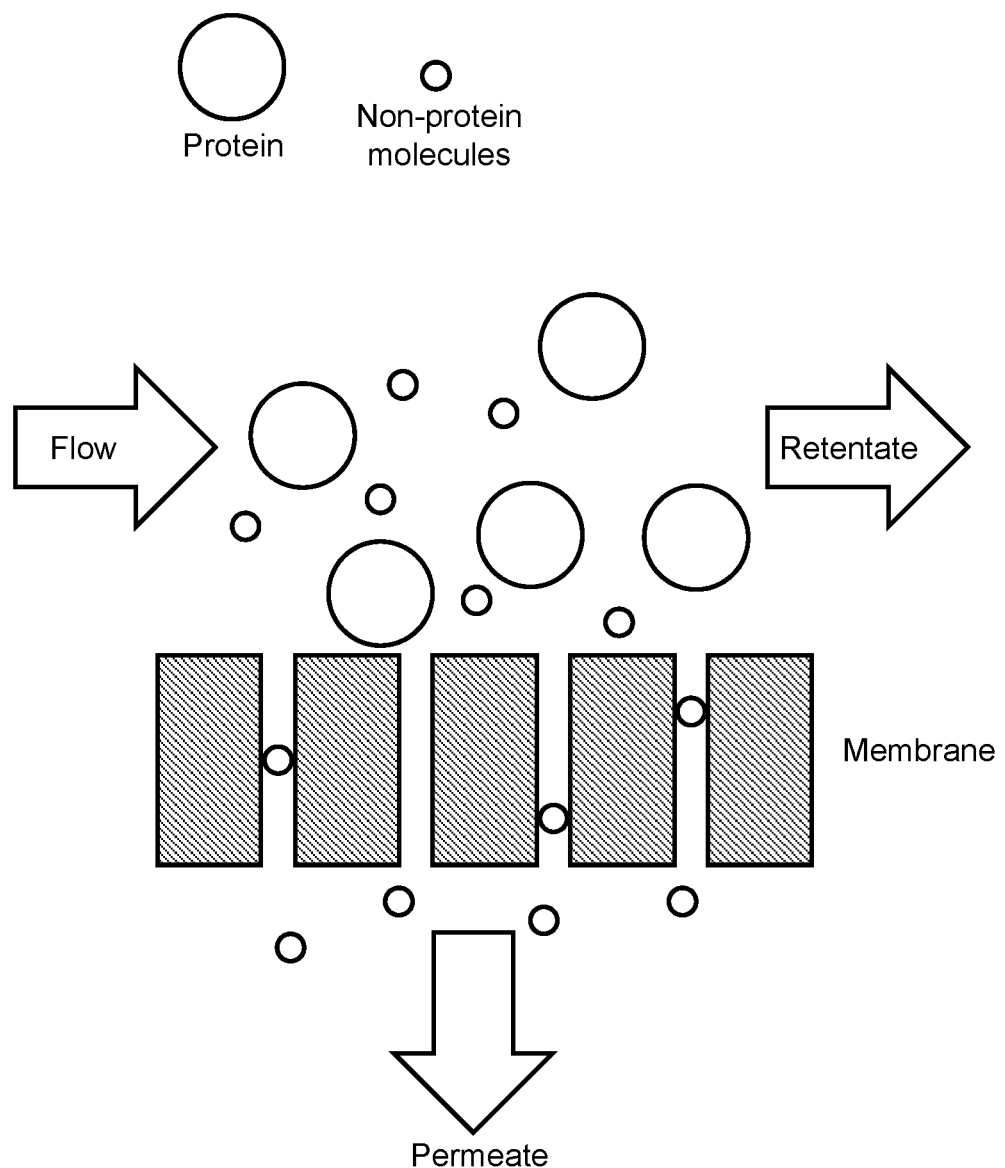
Figure 7:
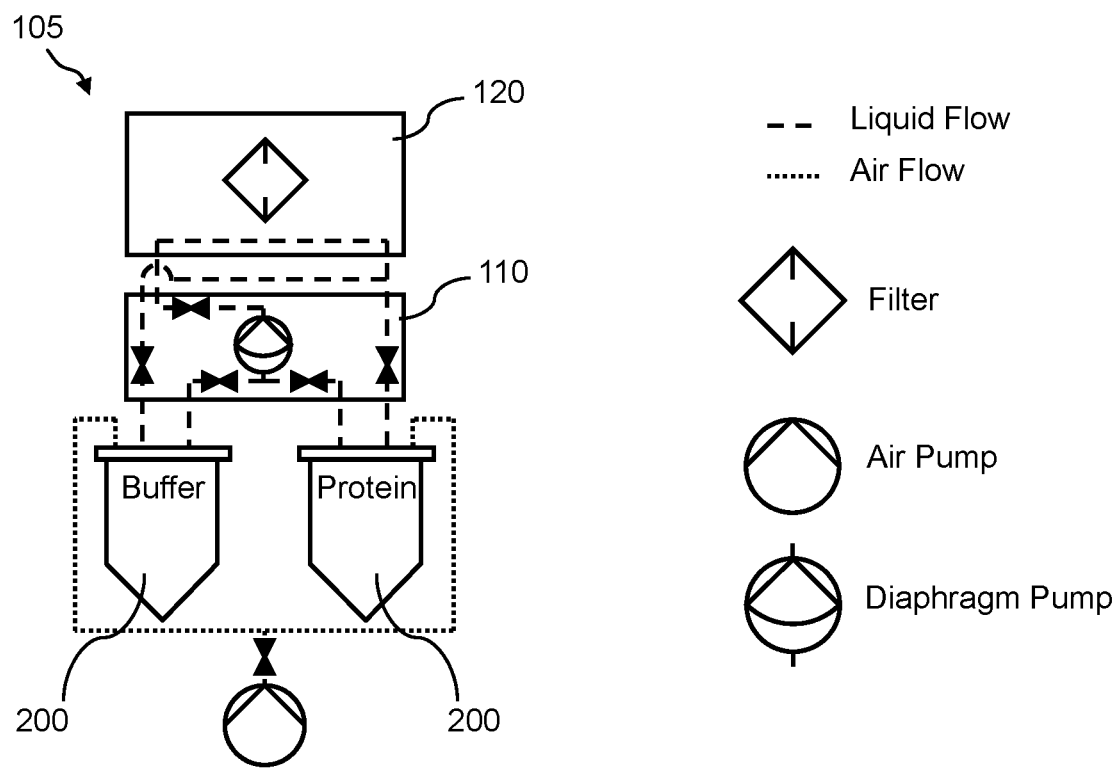
Figure 8A:
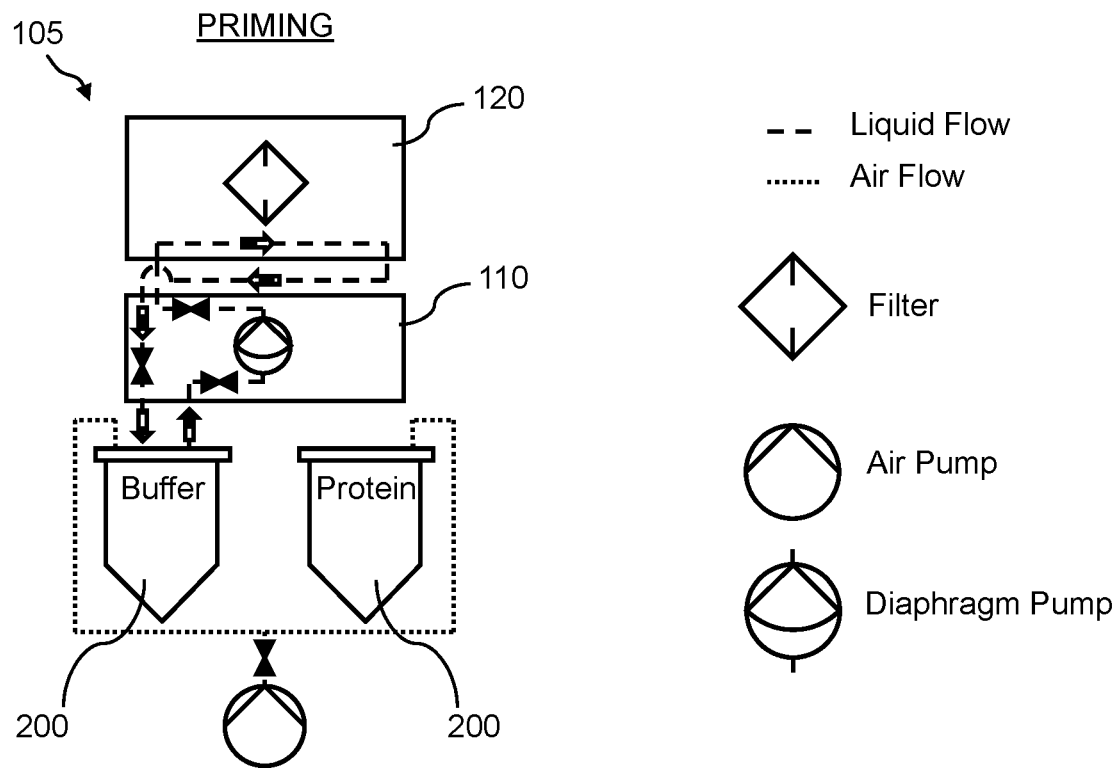
Figure 8B:
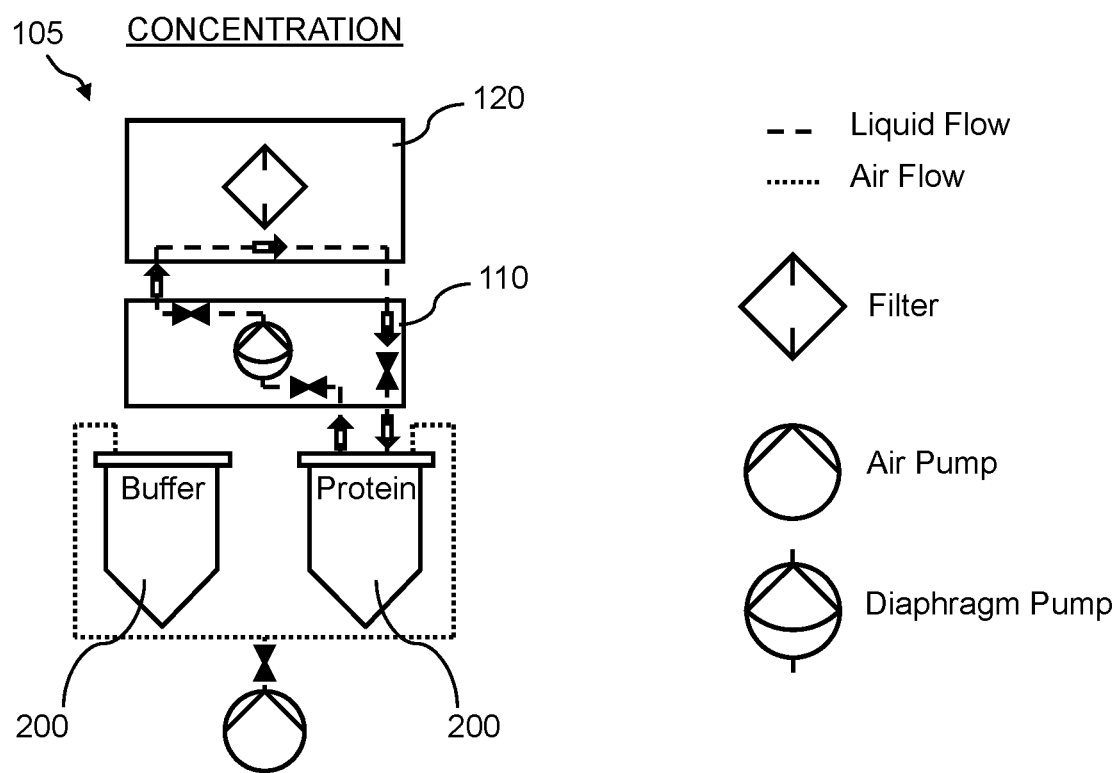
Figure 8C:
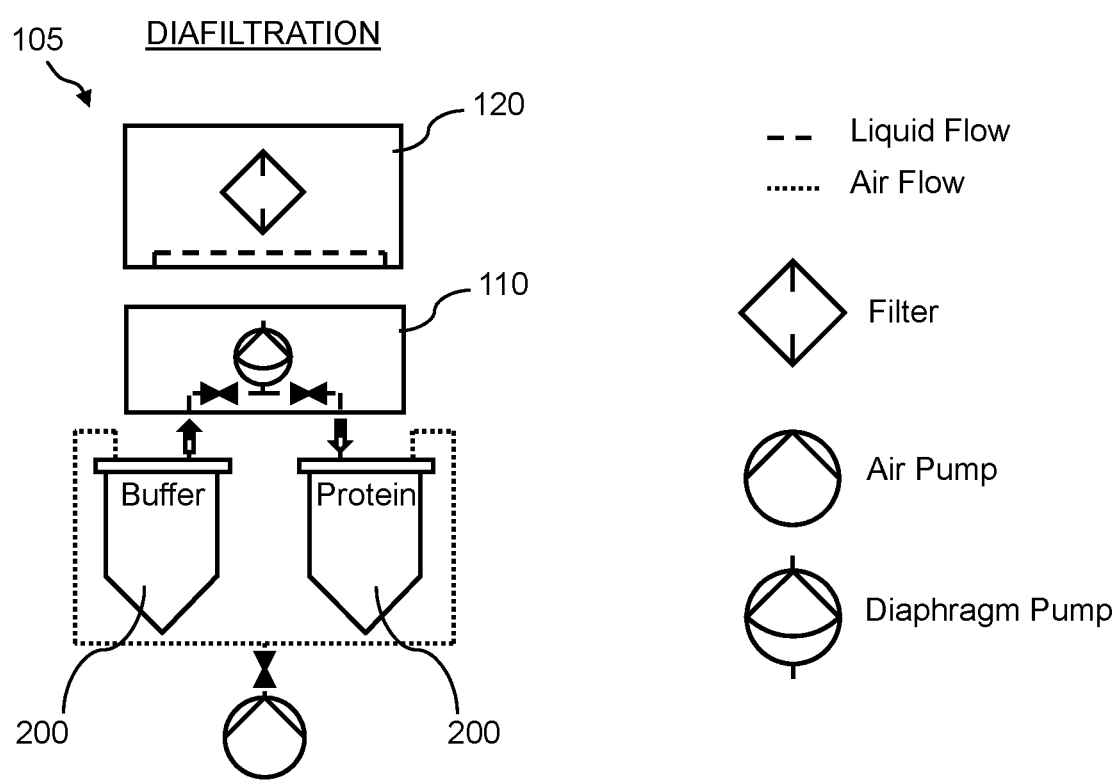
Figure 9:
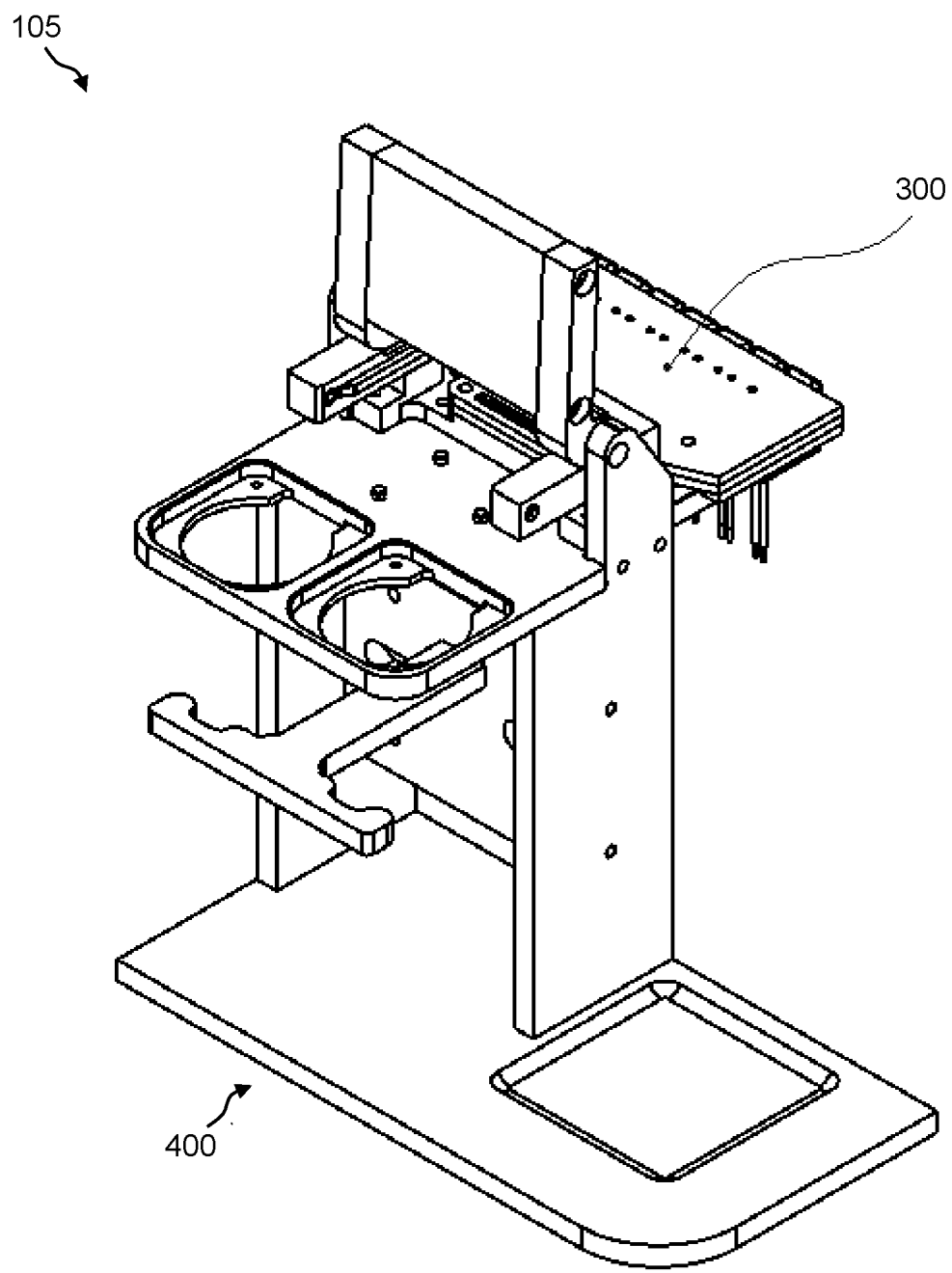
Figure 10:
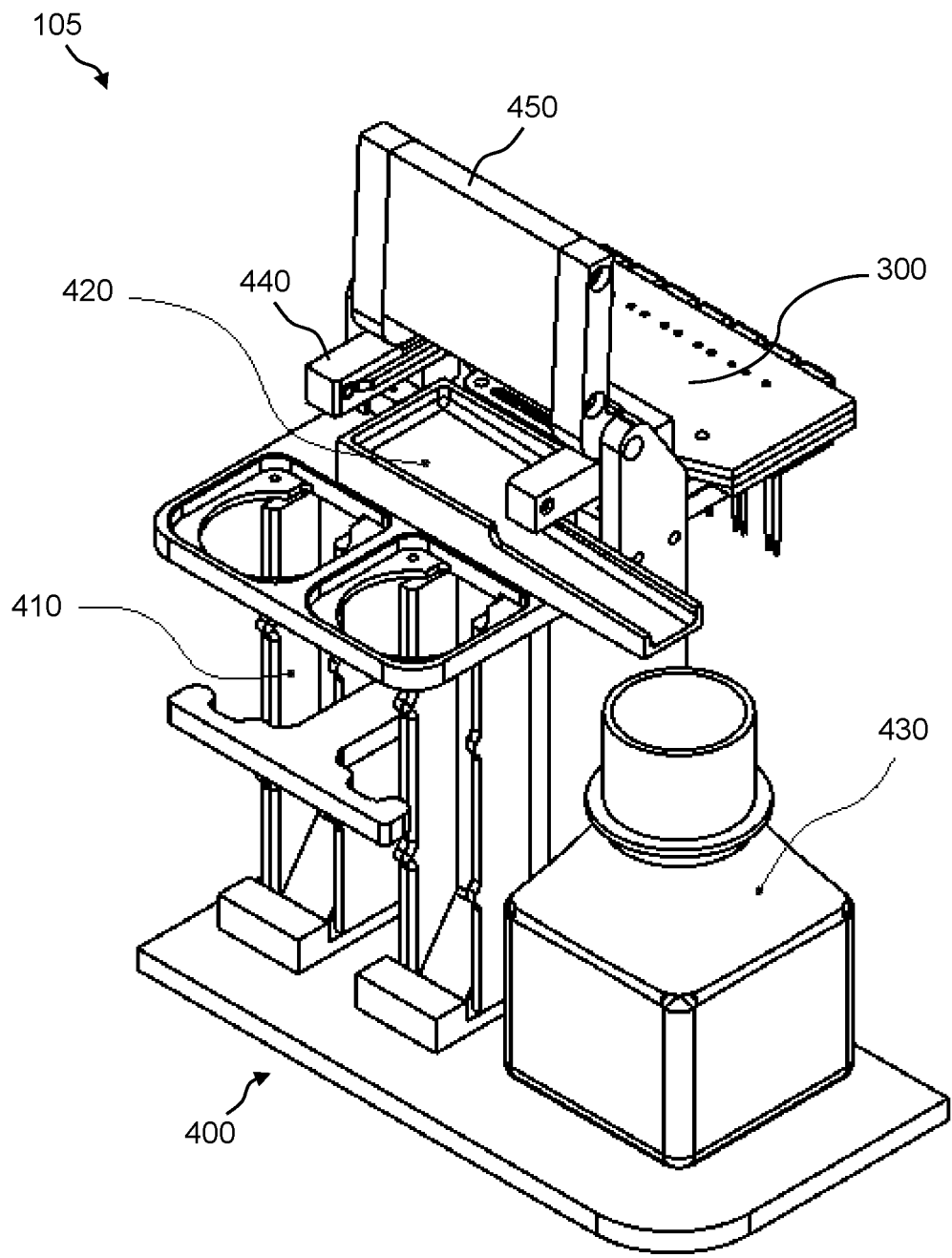
Figure 11:
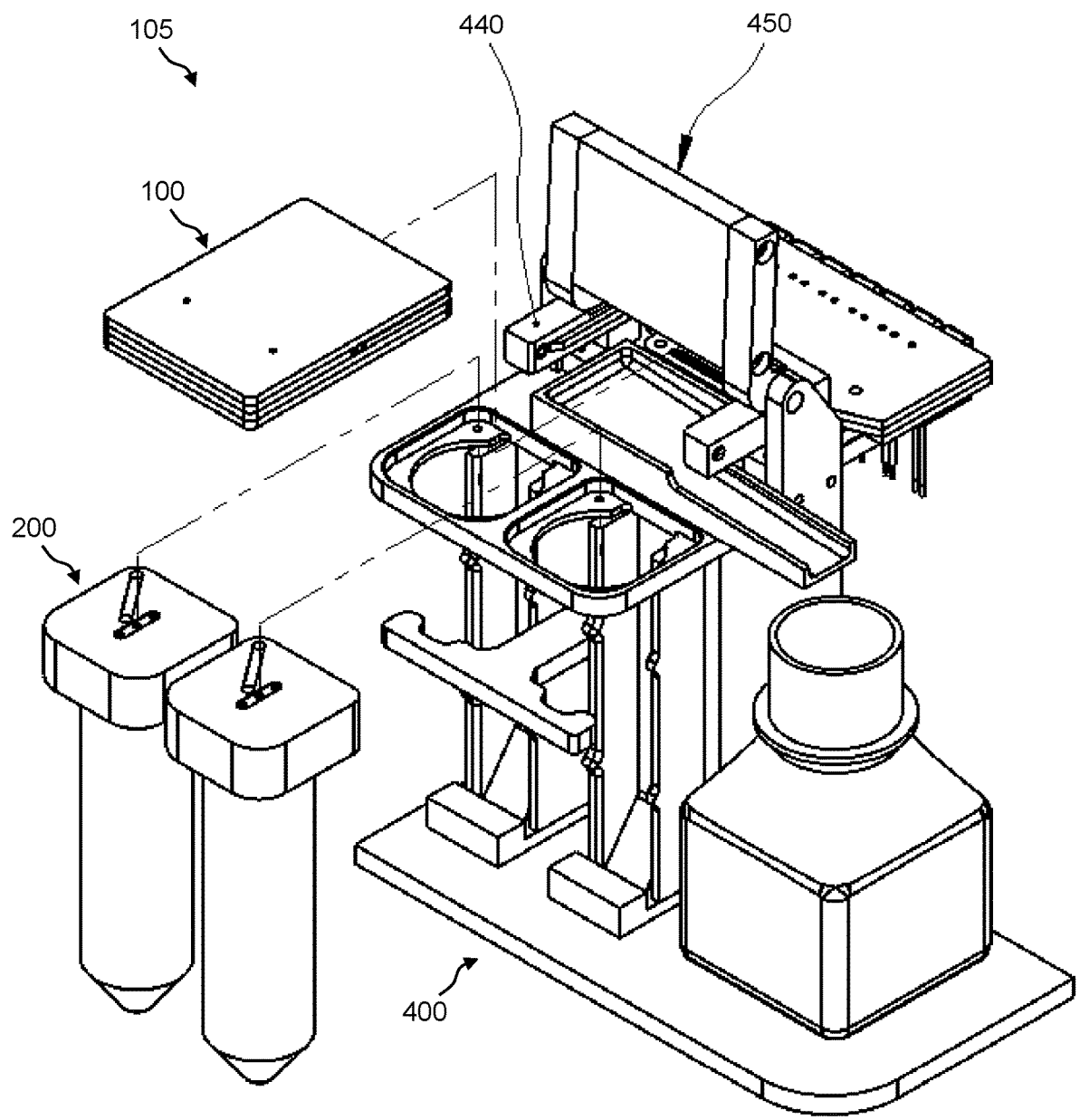
Figure 12:
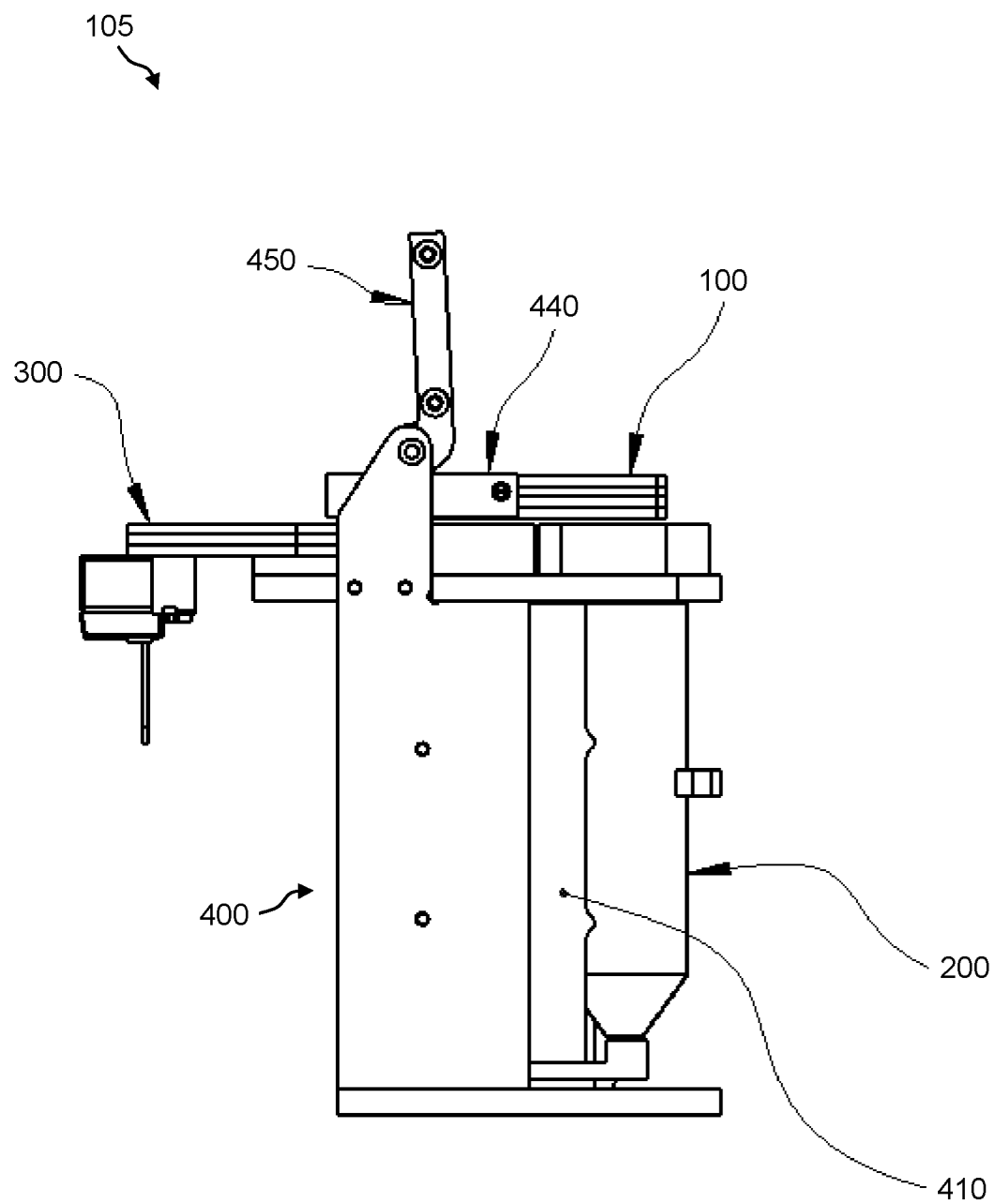
Figure 13:
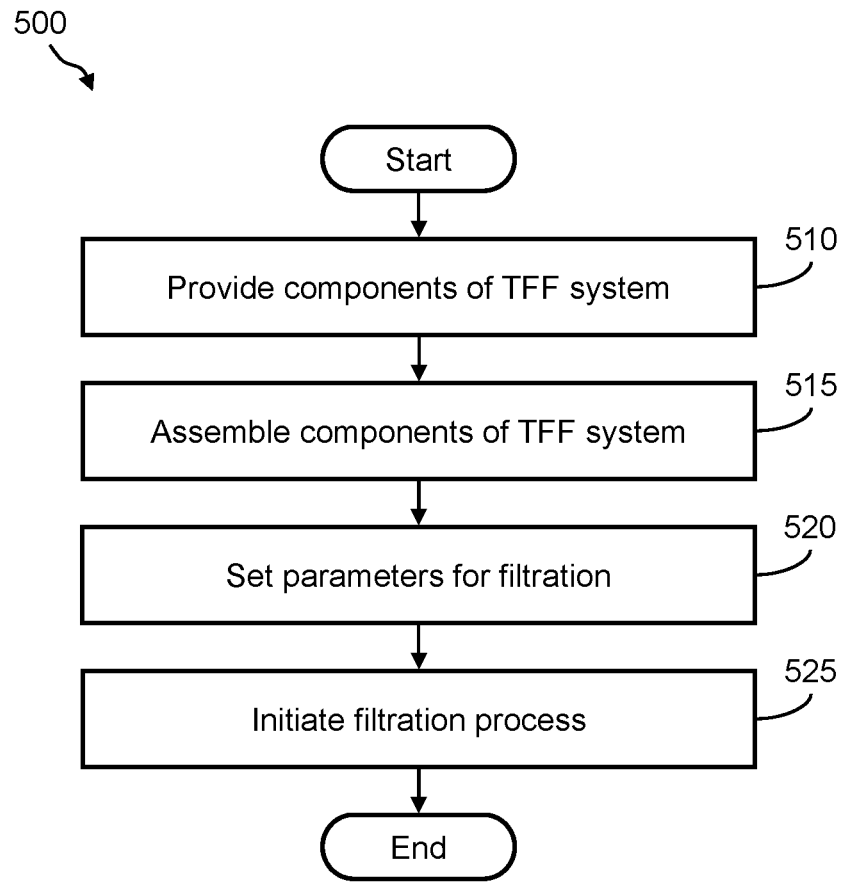
Figure 14:
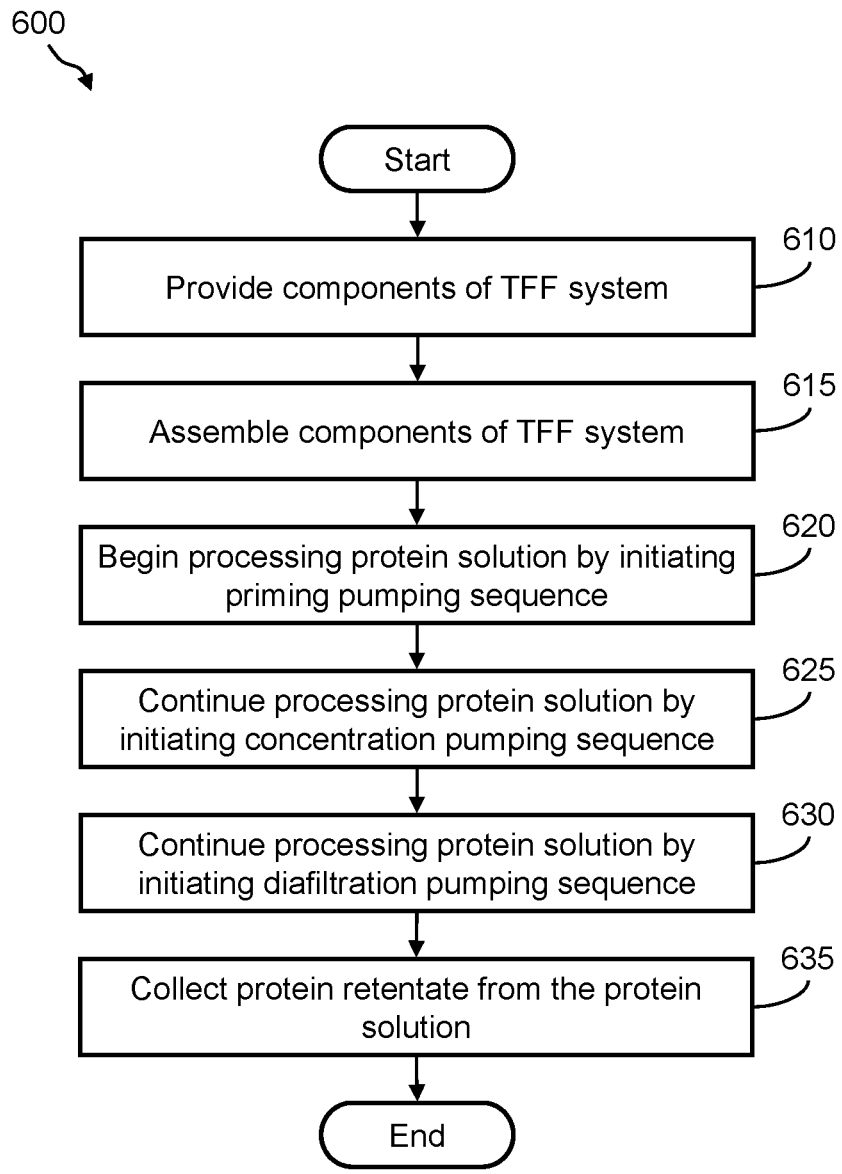

Having thus described the presently disclosed subject matter in general terms, reference will now be made to the accompanying Drawings, which are not necessarily drawn to scale, and wherein:

FIG. 1 and FIG. 2 illustrate a perspective view and an exploded view, respectively, of an example of the presently disclosed disposable TFF unit according to one embodiment of the present subject matter;

FIG. 3 illustrates an exploded view of the disposable TFF unit in combination with a pair of fluid reservoirs and an air supply assembly according to one embodiment of the present subject matter;

FIG. 4A and FIG. 4B illustrate a plan view and a cross-sectional view, respectively, of the presently disclosed disposable TFF unit according to one embodiment of the present subject matter;

FIG. 5 illustrates various views of an example of a diaphragm pump assembly of the presently disclosed disposable TFF unit according to one embodiment of the present subject matter;

FIG. 6 shows a schematic diagram of an example of the basic filtering operation of the disposable TFF unit and a TFF system according to one embodiment of the present subject matter;

FIG. 7 illustrates a block diagram of the presently disclosed TFF system that may include three modes of operation (or pumping sequences) for performing the filtration cycle according to one embodiment of the present subject matter;

FIG. 8A, FIG. 8B, and FIG. 8C illustrate block diagrams showing a priming pumping sequence, a concentration pumping sequence, and a diafiltration pumping sequence, respectively, of the TFF system shown in FIG. 7;

FIG. 9 illustrates a perspective view of a portion of the presently disclosed TFF system that includes an air supply assembly and a clamp assembly according to one embodiment of the present subject matter;

FIG. 10 illustrates a perspective view of a portion of the presently disclosed TFF system that includes an air supply assembly, a clamp assembly, volume sensors, a waste slide, and a waster container according to an embodiment of the present subject matter;

FIG. 11 illustrates an exploded view of all the components of the presently disclosed TFF system, which includes the presently disclosed disposable TFF unit according to one embodiment of the present subject matter;

FIG. 12 illustrates a side view of the presently disclosed TFF system when fully assembled, which includes the presently disclosed disposable TFF unit according to one embodiment of the present subject matter; and FIG. 13 and FIG. 14 illustrate flow diagrams of examples of methods of using the TFF system that includes the disposable TFF unit.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a tangential flow filtration (TFF) system and disposable TFF unit that includes an integrated pump apparatus. Namely, a TFF system is provided that includes a clamp assembly for integrating together a disposable TFF unit, two fluid reservoirs, and an air supply assembly. Further, the disposable TFF unit includes a diaphragm pump assembly and a concentration membrane.

An aspect of the presently disclosed TFF unit is that it is disposable and can be used with lower volumes to take advantage of the TFF method without the need to extensively clean after every use. Accordingly, the presently disclosed disposable TFF unit provides benefit over conventional TFF systems that are bulky, meant for relatively large volumes (>1L), and must be cleaned after every use.

Referring now to FIG. 1 and FIG. 2 is a perspective view and an exploded view, respectively, of an example of a disposable TFF unit 100 of the presently disclosed TFF system. As illustrated, a disposable TFF unit 100 includes an integrated diaphragm pump assembly 110 to concentrate a protein solution using an integrated concentration membrane 120 through the process known as tangential flow filtration (TFF). TFF is a process by which a protein solution is flowed past a membrane under pressure such that small, non-protein molecules are filtered out as a permeate, and proteins and a small amount of solution are kept in the system as retentate.

In one embodiment, the disposable TFF unit 100 may be made of multiple layers. For example, the disposable TFF unit 100 may include four layers 106 (i.e., layers 106a, 106b, 106c, 106d). In one example, the four layers 106 are acrylic layers. However, in other embodiments, the four layers 106 can be any material not inconsistent with the objectives of this disclosure. Further, disposable TFF unit 100 may be formed by laser-bonding the layers 106 together. For example, the laser-bonding process may use a dye that absorbs light of a specific wavelength output by a laser that causes the interface between two layers to heat up and become melted together.

Referring now to FIG. 2, the diaphragm pump assembly 110 and the concentration membrane 120 are provided between the outer layers 106a and 106d, and more specifically, between layer 106b and layer 106c, which are the middle two layers of the disposable TFF unit 100 between outer layers 106a and 106d. The layers 106 include interference features that create seals allowing air to actuate valves and the diaphragm, and pump liquid around the disposable TFF unit 100 and over the concentration membrane 120. In particular, the disposable TFF unit 100 may be formed of the multiple layers 106 that have various air channels 101, various fluidic channels 102, the concentration membrane 120, and the diaphragm pump assembly 110. The diaphragm pump assembly 110 (see FIG. 5) may include an actuated valve component, including a cluster of air actuated valves 111, and a diaphragm component, including diaphragm 112, for pumping the liquids. Input/output flow ports (through-holes) 103 may be included for connections for air flow control. Further, the layers 106 may include input/output flow ports (through-holes) 104 that can be used for fluid ports for liquid flow control.

Referring now to FIG. 3 is an exploded view of one embodiment of the disposable TFF unit 100 in combination with a fluid reservoir assembly, including a pair of fluid reservoirs 200, and an air supply assembly 300. In this example, the disposable TFF unit 100 connects to the air supply assembly 300 at one end and to the two fluid reservoirs 200 at an opposing end. The fluid reservoirs 200 may be, for example, two 50 mL falcon tubes. In one example, one fluid reservoir 200 may contain the protein solution, while the other fluid reservoir 200 may contain a buffer solution. Each of the fluid reservoirs 200 may include a custom cap 210, a standard falcon tube 220, and small liquid tubes, not shown, that mount in the cap 210 and extend downward into the liquid. Two types of gaskets (e.g., a tube gasket 230 and an air supply gasket 320) may be used to seal the connections between the disposable TFF unit 100 and the fluid reservoirs 200 and the air supply assembly 300. The air supply assembly 300 may include an air supply unit 310 and multiple solenoids 330 that are used to actuate various parts of the disposable TFF unit 100.

Referring now to FIG. 4A and FIG. 4B is a plan view and a cross-sectional view, respectively, of the disposable TFF unit 100. Namely, FIG. 4B is a cross-sectional view of the disposable TFF unit 100 taken along line A-A of FIG. 4A. Referring now also to FIG. 5 is various views of an example of the diaphragm pump assembly 110. The diaphragm pump assembly 110 includes the cluster of air actuated valves 111 and the diaphragm 112, as shown in FIG. 5. For example, the diaphragm pump assembly 110 may include a cluster of air actuated valves 111 (e.g., five air actuated valves 111) and one diaphragm 112. However, a wide variety of combinations of air actuated valves 111 and diaphragms 112 can be used to allow for more or less control over how liquids may be circulated within the disposable TFF unit 100. For example, the presence of multiple diaphragms 112 for generating the pumping action may provide more consistent flow as compared to using a single diaphragm 112 only.

In operation, one embodiment of the disposable TFF unit 100 may pump liquid using air-actuated positive displacement. The bank of solenoids 330 (see FIG. 3) may be used to apply positive or negative pressure through the air supply unit 310 to one side of the air actuated valves 111 and diaphragm 112 to open or close them. The air actuated valves 111 may be small areas of the cluster, which allow or prohibit flow between two flow ports (through-holes). In one embodiment, three actuated valves 111 may be clustered at one end of the diaphragm pump assembly 110, and two actuated valves 111 may be clustered at an opposing end. The diaphragm 112 may be a domed section larger than the actuated valves 111 of the diaphragm pump assembly 110, which aspirates or dispenses liquid into and out of a chamber 107 (see FIG. 4) adjacent to the diaphragm 112 and through a flow port (through-hole). The driving air pressure applied to the air actuated valves 111 and the diaphragm 112 through the air channels 101 is higher than the internal pressure so as to create an equal pressure differential between the vacuum, internal pressure, and driving pressure. Different sequences of opening and closing the air actuated valves 111 and the diaphragm 112 can be used to pump liquid from either fluid reservoir 200 in various ways throughout the disposable TFF unit 100 via the fluidic channels 102.

Further, FIG. 6 shows a schematic diagram of an example of the basic filtering operation supported by the disposable TFF unit 100 and/or a TFF system 105 that is described hereinbelow with reference to FIG. 7 through FIG. 12. In FIG. 6, the combination of circulation and higher internal pressure than the atmosphere forces an amount of the solution through a membrane, leaving the protein and a remaining amount of solution behind. The solution that passes through the membrane is called the "permeate." The remaining amount of solution that does not pass through the membrane is called the "retentate."

FIG. 7 shows a block diagram of one embodiment of the TFF system 105 that includes the overall layout of the diaphragm pump assembly 110, the concentration membrane 120, the protein fluid reservoir 200, and the buffer fluid reservoir 200. Further, the TFF system 105 that may provide three modes of operation (or pumping sequences) for performing the filtration cycle. For example, FIG. 8A, FIG. 8B, and FIG. 8C show block diagrams showing a priming pumping sequence, a concentration pumping sequence, and a diafiltration pumping sequence, respectively, of the TFF system 105 shown in FIG. 7. In FIG. 8A, FIG. 8B, and FIG. 8C, the arrows show the direction of flow in each of the pumping sequences.

The solution from the two fluid reservoirs 200 may be pumped in a multitude of ways. An air channel 101 from the air supply unit 310 may pressurize the entire liquid system, (i.e., the falcon tubes 220 and the disposable TFF unit 100) to a desired pressure. The combination of circulation and higher internal pressure than the atmosphere forces an amount of the solution through the membrane (i.e., the permeate), leaving the protein and a remaining amount of solution (i.e., the retentate), as previously shown and described in FIG. 6.

Referring now again to FIG. 3, there may be two liquid connections and one air connection to each of the caps 210. The caps 210 of the fluid reservoirs 200 each typically has two small diameter tubes (not shown) mounted in it that extend downward into the liquid. Generally, one connection/tube is used for aspirating liquid from the fluid reservoir 200 and the other is used to return liquid to the fluid reservoir 200. Depending on the specific pumping sequence, these steps may vary. The air connection to each tube may be common between them and pressurizes the air and liquid in both tubes, which in turn pressurizes the channels in the disposable TFF unit 100.

Generally, one fluid reservoir 200 will contain protein solution, and the other fluid reservoir 200 will contain buffer solution, but both fluid reservoirs 200 could contain protein solution. The buffer solution may be used to initially prime (see FIG. 8A) the TFF system 105 to remove air bubbles from the fluidic channels 102. The protein solution may be circulated under pressure until it has been concentrated (see FIG. 8B) to a desired amount. The buffer solution may then be used to diafiltrate or dilute (see FIG. 8C) the protein solution before another concentration cycle, if desired. Otherwise, the TFF system 105 will pump the remaining protein solution back into the protein fluid reservoir 200, and notify the user the cycle is finished. In some embodiments, disposable TFF unit 100 is intended to be used for up to three 50 mL concentration cycles of the same type of protein solution, although in other embodiments, the disposable TFF unit 100 can be used for up to four, five, or six 50 mL concentration cycles of the same type of protein solution.

After being so used, the disposable TFF unit 100 may be discarded, and the caps 210 may either be discarded or cleaned.

Referring now to FIG. 9, FIG. 10, FIG. 11, and FIG. 12, an example of the TFF system 105 that includes the presently disclosed disposable TFF unit 100 is shown. FIG. 9 is a perspective view of a portion of the TFF system 105 that includes the air supply assembly 300 and a clamp assembly 400. FIG. 10 is a perspective view of a portion of the TFF system 105 that includes the air supply assembly 300 and the clamp assembly 400, and that further includes one or more volume sensors 410, a waste slide 420, and a waste container 430. FIG. 11 is an exploded view of all the components of one embodiment of the TFF system 105. FIG. 12 is a side view of one embodiment the TFF system 105 when fully assembled.

The TFF system 105 may include the clamp assembly 400, the pressure and vacuum pumps, electronics, a touch screen to set parameters for operation, as well as other components not shown. In one embodiment, the clamp assembly 400 may be a consumable clamp assembly.

The clamp assembly 400 may further be an aluminum structure used to hold the two fluid reservoirs 200, the disposable TFF unit 100, the air supply assembly 300, the volume sensors 410 for measuring liquid level in the fluid reservoirs 200, and the waste slide 420 for collecting the permeate, wherein the waste slide 420 channels the permeate into the waste container 430.

FIG. 9, FIG. 10, FIG. 11, and FIG. 12 show a progression of components in the clamp assembly 400 in order to clarify the number of components of one embodiment of the overall TFF system 105. FIG. 9 shows the clamp assembly 400 and air supply assembly 300. FIG. 10 shows volume sensors 410, a unit holder 440, a clamp handle 450, a waste slide 420, and waste container 430 added to the assembly. FIG. 11 shows the fluid reservoirs 200 and disposable TFF unit 100, which are preferably placed into the clamp assembly 400 in that order. As shown in FIG. 12, the disposable TFF unit 100 may be held in the unit holder 440 using matching slots that keep the disposable TFF unit 100 aligned. The clamp handle 450 may then be rotated 90 degrees toward the back of the clamp assembly 400. Rotating the clamp handle 450 forces the unit holder 440, and thus the disposable TFF unit 100, downward using a cam type actuation so that the disposable TFF unit 100 contacts and seals against the air supply assembly 300 and the fluid reservoirs 200. The unit holder 440 may be spring loaded so that when the clamp handle 450 is pulled up the unit holder 440 will spring back up.

Referring now to FIG. 13 is a flow diagram of an example of a method of using the TFF system 105; namely, a method 500. Method 500 may include, but is not limited to, one or more of the followings steps.

At a step 510, the components of the TFF system 105 are provided. For example, the disposable TFF unit 100, the fluid reservoirs 200, the air supply assembly 300, and the clamp assembly 400 that further includes the volume sensors 410, the waste slide 420, and the waste container 430 are provided. In one example, one fluid reservoir 200 contains a protein solution, while the other fluid reservoir 200 contains a buffer solution. In another example, both fluid reservoirs 200 contain protein solution.

At a step 515, the components of the TFF system 105 are assembled. For example, the user inserts the two fluid reservoirs 200 into the clamp assembly 400. Next, the user inserts the disposable TFF unit 100 into the clamp assembly 400. Next, the user engages the clamp handle 450 to lock the disposable TFF unit 100 into the clamp assembly 400. Next, the user operatively connects the TFF disposable unit 100 to the air supply assembly 300 and the fluid reservoir 200.

At a step 520, the user interacts with a user interface, such as a touch screen (not shown), of the TFF system 105 to set the parameters for filtration.

At a step 525, the user interacts with the user interface of the TFF system 105 to initiate the filtration process.

Upon the completion of method 500, the user can reverse the order of operations in the step 515 to remove the components of the TFF system 105 and either discard the disposable TFF unit 100 or set it aside for later use.

Referring now to FIG. 14 is a flow diagram of another example of a method of using the TFF system 105; namely, a method 600. Method 600 may include, but is not limited to, one or more of the followings steps.

At a step 610, the components of the TFF system 105 are provided. For example, the disposable TFF unit 100, the fluid reservoirs 200, the air supply assembly 300, and the clamp assembly 400 that further includes the volume sensors 410, the waste slide 420, and the waste container 430 are provided. In one example, one fluid reservoir 200 contains a protein solution, while the other fluid reservoir 200 contains a buffer solution. In another example, both fluid reservoirs 200 contain protein solution.

At a step 615, the components of the TFF system 105 are assembled. For example, the user inserts the two fluid reservoirs 200 into the clamp assembly 400. Next, the user inserts the disposable TFF unit 100 into the clamp assembly 400. Next, the user engages the clamp handle 450 to lock the disposable TFF unit 100 into the clamp assembly 400. Next, the user operatively connects the TFF disposable unit 100 to the air supply assembly 300 and the fluid reservoir 200.

At a step 620, processing of the protein solution begins by initiating the priming pumping sequence as shown, for example, in FIG. 8A.

At a step 625, processing of the protein solution continues by initiating the concentration pumping sequence as shown, for example, in FIG. 8B.

At a step 630, processing of the protein solution continues by initiating the diafiltration pumping sequence as shown, for example, in FIG. 8C.

At a step 635, the protein retentate is collected from the protein solution.

Upon the completion of method 600, the user can reverse the order of operations in the step 615 to remove the components of the TFF system 105 and either discard the disposable TFF unit 100 or set it aside for later use.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A tangential flow filtration (TFF) system for concentrating a protein solution comprising:
   a TFF unit having a diaphragm pump assembly and a concentration membrane, wherein the TFF unit has multiple layers including two middle layers, wherein the diaphragm pump assembly and the concentration membrane are between the two middle layers of the multiple layers, and wherein the multiple layers of the TFF unit have air channels, fluidic channels, and flow ports for liquid flow control and for air flow control,
   an air supply assembly operatively connected to the TFF unit; and
   a fluid reservoir assembly operatively connected to the TFF unit.

2. The TFF system as recited in claim 1, wherein the TFF unit is disposable and adapted for use up to three 50 mL concentration cycles of the same protein containing solution.

3. The TFF system as recited in claim 1, wherein the air supply assembly is connected to the TFF unit at one end, and the fluid reservoir assembly is connected to the TFF unit at an opposite end.

4. The TFF system as recited in claim 1 wherein a chamber is formed between the multiple layers adjacent to the diaphragm pump assembly.

5. The TFF system as recited in claim 1, wherein the multiple layers include four layers that are laser bonded, the four layers having an outermost two layers and the two middle layers between the outermost two layers.

6. The TFF system as recited in claim 1, wherein the diaphragm pump assembly includes a valve component and a diaphragm component adapted to aspirate or dispense protein containing solution through the flow ports.

7. The TFF system as recited in claim 6, wherein the valve component has clusters of air actuated valves, including a cluster of three air actuated valves at one end of the diaphragm pump assembly and a cluster of two air actuated valves at an opposing end of the diaphragm pump assembly.

8. The TFF system as recited in claim 7, wherein the diaphragm component is a diaphragm that is a domed section larger than the valve component.

9. The TFF system as recited in claim 6, wherein the diaphragm component includes multiple diaphragms.

10. The TFF system as recited in claim 6, wherein the air supply assembly includes an air supply unit and a bank of solenoids operatively connected to the air supply unit to apply positive or negative pressure to the diaphragm pump assembly.

11. The TFF system as recited in claim 1, wherein the fluid reservoir assembly includes two fluid reservoirs, one for containing protein containing solution and another for containing a buffer solution.

12. The TFF system as recited in claim 11, wherein each of the two fluid reservoirs includes a cap mounted with a liquid flow connector and an air flow connector.

13. The TFF system as recited in claim 12, wherein the liquid flow connector includes two tubes that extend downward into the contained liquid, one of the two tubes used to aspirate liquid from the fluid reservoir, and the other of the two tubes used to return liquid to the fluid reservoir, and wherein the air flow connector is common between the two fluid reservoirs.

14. The TFF system as recited in claim 1, further comprising a clamp assembly for holding the TFF unit, the air supply assembly, and the fluid reservoir assembly.

15. The TFF system as recited in claim 14, further comprising a volume sensor for measuring liquid level in the fluid reservoir assembly, a waste slide adapted to channel permeate, and a waste container connected to the waste slide and being adapted to collect the channeled permeate.

16. The TFF system as recited in claim 15, further comprising a unit holder and a clamp handle, the unit holder having slots for aligning the TFF unit, and the clamp handle disposed proximally to the unit holder such that rotation of the clamp handle forces the unit holder and the TFF unit into the clamp assembly so that the TFF unit becomes connected to and sealed with the fluid reservoir assembly and the air supply assembly.

* * * * *